United States Patent [19]

Venturello et al.

[11] Patent Number: 5,071,584
[45] Date of Patent: Dec. 10, 1991

[54] HETEROCYCLIC PEROXYCARBOXYLIC ACIDS USEFUL AS BLEACHES IN DETERGENTS

[75] Inventors: Carlo Venturello, Novara; Claudio Cavallotti, Milan, both of Italy

[73] Assignee: Ausimont S.p.A., Milan, Italy

[21] Appl. No.: 593,379

[22] Filed: Oct. 2, 1990

Related U.S. Application Data

[63] Continuation of Ser. No. 219,361, Jul. 15, 1988, abandoned.

[30] Foreign Application Priority Data

Jul. 20, 1987 [IT] Italy ................. 21345 A/87

[51] Int. Cl.$^5$ ............ C07C 409/06; C11D 3/28; C11D 3/395; D06L 3/02
[52] U.S. Cl. ................. 252/102; 252/186.42; 252/524; 252/542; 546/245; 562/2
[58] Field of Search .......... 252/102, 186.42, 524, 252/542; 560/502 R

[56] References Cited

U.S. PATENT DOCUMENTS

| | | | |
|---|---|---|---|
| 4,087,455 | 5/1978 | Prescher | 260/502 R |
| 4,168,274 | 9/1979 | Hildon | 549/525 |
| 4,199,466 | 4/1980 | Benson | 252/102 |
| 4,403,994 | 9/1983 | Hignett | 8/111 |
| 4,606,838 | 8/1986 | Burns | 252/94 |
| 4,634,551 | 1/1987 | Burns | 252/102 |
| 4,751,015 | 6/1988 | Humphreys | 252/99 |
| 4,820,437 | 4/1989 | Akabane | 252/102 |

FOREIGN PATENT DOCUMENTS 0233476 8/1987 European Pat. Off. .

Primary Examiner—Paul Lieberman
Assistant Examiner—Kevin D. McCarthy
Attorney, Agent, or Firm—Morgan & Finnegan

[57] ABSTRACT

Nitrogen-containing heterocyclic (poly)peroxycarboxylic acids having the formula:

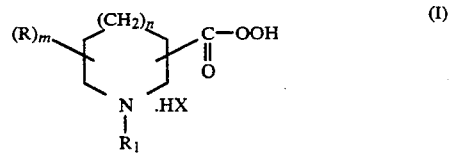

wherein:
R and $R_1$ represent, independently of each other, a hydrogen atom or a straight or branched alkyl, (hetero)cycloalkyl, (hetero)aryl, alkylaryl or arylalkyl group,
optionally substituted, a carboxylic group, or any other substituent which is non-reactive in the presence of the active oxygen of the peroxycarboxylic group;
n is an integer selected from 0, 1 and 2;
m is an integer selected from 1, 2 and 3; and
X represents an acidic anion selected from $HSO_4^-$ and $CH_3SO_3-$ and wherein the heterocyclic ring may be condensed with at least one further (hetero)aromatic or (hetero)cycloalkylic ring.

23 Claims, No Drawings

HETEROCYCLIC PEROXYCARBOXYLIC ACIDS USEFUL AS BLEACHES IN DETERGENTS

This is a continuation of co-pending application Ser. No. 07/219,361, filed on July 15, 1988.

DESCRIPTION OF THE INVENTION

This invention relates to new organic (poly)peroxyacids which may be referred to as N-hetero-cyclic (poly)peroxycarboxylic acids, and to the manufacturing process therefor.

In particular, the invention relates to heterocyclic (poly)peroxycarboxylic acids containing nitrogen in the ring and having formula (I):

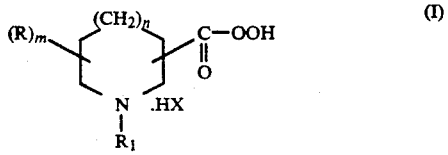

wherein:
- R and $R_1$ represent, independently of each other, a hydrogen atom or a straight or branched alkyl, (hetero)cycloalkyl, (hetero)aryl, alkylaryl or arylalkyl group, optionally substituted, a carboxylic group, or any other substituent which is non-reactive in the presence of the active oxygen of the peroxycarboxylic group;
- n is an integer selected from 0, 1 and 2;
- m is an integer selected from 1, 2 and 3; and
- X represents an acidic anion selected from $HSO_4^-$ and $CH_3SO_3$ and wherein the heterocyclic ring may be condensed with at least one further (hetero)aromatic or (hetero)cycloalkylic ring.

The heterocyclic peroxycarboxy compounds having the formula (I) above are new, and represent a new class of highly interesting products.

They, in fact, may find a general use, similarly to already known peroxyacids, in the field of plastics (as a polymerization starter or as an oxidizing agent for olefin epoxidation or hydroxylation) and in many other oxidative processes in the field of fine chemistry.

In a very peculiar way, however, the heterocyclic (poly)peroxycarboxylic acids having the formula (I) above find a particularly efficacious application in the field of bleaching, in the detergency industry.

The organic peroxyacids in past years generally aroused an increasing interest in the industrial field, due, among others, to their excellent behavior as bleaching agents in formulations for medium-low temperature washing, the advantages being more and more widespread also on the basis of energy-saving considerations.

Much prior art deals with organic peroxyacid compounds endowed with bleaching activity, with thermal stability and storage stability, these latter features being essential for industrial purposes and for a widespread application of such compounds.

Therefore many mono- or di-peroxycarboxylic (aliphatic or carbocyclic) organic peroxyacids are known and used, among others, in the field of detergency.

Already-described peroxycarboxylic acids are, e.g., diperoxydodecanedioic acid, monoperoxyphthalic acid, diperazelaic acid, substituted diperoxyglutaric and adipic acids, and so forth.

Applicants are not aware of any previous heterocyclic (poly)peroxycarboxylic acid having formula (I), nor of any previous process for the manufacture thereof.

The traditional process involves an oxidation of the substrate (an organic acid, anhydride or ester) with a concentrated solution of hydrogen peroxide, in concentrated $H_2SO_4$ or $CH_3SO_3H$.

The strong acidity of the reaction medium and the presence in the substrate of a salifiable nitrogen atom having a basic character, give such substrate a high solubility in the acidic medium. Said high solubility, however, makes it impossi-ble to resort to any of the traditional processes for isolation of the -peroxycarboxylic acid derivative occasionally formed during the oxidation reaction with hydrogen peroxide, by precipitation or by extraction methods with organic solvents.

Surprisingly, in accordance with the present invention it has been discovered, on the contrary, that the heterocyclic (poly)peroxycarboxylic acids having formula (I), salified (on the nitrogen atom) by means of a sulphate or methanesulphonate anion, may be obtained in a stable form by a novel and simpler process, and which therefore is also an object of this invention.

One object of the present invention is to provide, as a new series of compounds, the heterocyclic (poly)peroxycarboxylic acids having the above formula (I).

Another object is to provide a cheap process for the preparation of said peroxycarboxylic acids having the above formula (I), in a stable form.

A further object consists in the use of said heterocyclic peroxycarboxylic acids as a bleaching agent in detergent formulations, especially when intended for low-medium temperature washing.

These, and still other objects of the invention are achieved via the heterocyclic peroxycarboxylic acids having the formula (I) and via a corresponding manufacturing process, characterized in that a substrate, consisting of a heterocyclic (poly)carboxylic acid containing a nitrogen atom in the ring, and/or its anhydride and/or its lower alkyl esters, corresponding to the desired peroxycarboxylic acids having formula (1), is concentrated $H_2O_2$ (by working in a medium selected from concentrated $H_2SO_4$ and $CH_3SO_3H$), and in that the peroxycarboxylic acid (I) is then separated from the reaction mixture by the addition of an organic solvent selected from the class consisting of tetrahydrofuran and ethyl acetate.

In this way one may very easily obtain the peroxycarboxylic acids having formula (1), generally in the form of stable solids, salified (on their nitrogen atom) with a sulphate or methanesulphonate anion derived from the reaction medium, due to their insolubilization in the reaction medium as a consequence of the presence of the said solvents.

In a more detailed form, the novel process of the present invention resides in the peroxycarboxylation of a substrate consisting or consisting essentially of a (poly)acid, or anhydride or ester thereof, corresponding to the desired (poly)peroxycarboxylic acid of formula (I), in a medium acidified by concentrated $H_2SO_4$ or $CH_3SO_3H$, with $H_2O_2$ and in the subsequent addition, at the reaction end, of a suitable organic solvent, which is not miscible with the desired product and which is capable, on the contrary, of completely dissolving the acidic reaction medium (concentrated $H_2SO_4$ or $CH_3SO_3H$), as well as the excess of $H_2O_2$ with the reaction water. All this involves the consequent separation, by insolubilization, of the (poly)peroxycarboxylic acid having formula (I) which ipitates, usually in a stable solid form. The thus-obtained product is then filtered, washed with the solvent, dried and so forth according to per se known techniques.

As already stated, the substrate consists of, the heterocyclic (poly)carboxylic acid corresponding to the desired (poly)peroxycarboxylic acid of formula (I); it can furthermore be used in the form of its corresponding lower (straight or branched) ($C_1$–$C_5$)-alkyl ester or, when two adjacent carboxylic groups (R=COOH) are present, also in the form of its corresponding anhydride. These compounds are known and/or can be prepared according to conventional technicques and/or available in the market.

In said formula (I), R and/or $R_1$ consist of a linear or branched alkyl, (hetero)-alkyl, (hetero)-cycloalkyl; alkylaryl or aryl-alkyl group, containing an overall number of up to 10 carbon atoms; in the heterocyclic groups other N or O atoms may be present preferably in the meta-or para-position with respect to the N heteroatom.

Said groups may in turn bear one or more substituent atoms or groups, equal to or different from each other, inert under the reaction conditions under which the preparation takes place, such as e.g., F or Cl atoms, $NO_2$ groups, lower alkoxy groups, and so forth.

As an alternative, R and/or $R_1$ may consist of any other substituent which does not react with the active oxygen of the peroxycarboxylic group; e.g., a carboxylic group, an F atom, a Cl atom, an $NO_2$ group, lower ($C_1$–$C_5$)- alkoxy groups, and so forth.

Finally, the heterocyclic moiety may be condensed with at least one other (hetero)aromatic or (hetero)cycloalkyl ring, in the form of e.g., quinolinic, isoquinolinic, pyridoindolic groups and so forth.

Starting substrates for obtaining the corresponding (hetero)cyclic perox-ycarboxylic acids having formula (I) are, for instance: 4-piperidine-carboxylic acid, 2,4-piperidinedicarboxylic acid, 3-piperidine-carboxylic acid, 2,3-piperidine-dicarboxylic acid and its anhydride, 2,5-piperidinedicarboxylic acid, 3, 5-piperidine-dicarboxylic acid, the ethyl ester of 4-piperidine-carboxylic acid, 2,6-dihydroxy-4-piperidine-carboxylic acid, 6-isobutyl-3-piperidine-carboxylic acid, 6-methyl-3-piperidine-carboxylic acid, 6-fluoromethyl-3-piperidine-carboxylic acid, 5-p-tolyl-4-piperidine-carboxylic acid, 5-benzyl-3-piperidine-carboxylic acid, 5-chloro-4-piperidine-carboxylic acid, and 3-pyrrolidine-carboxylic acid.

When R=COOH, preferably in a non-ortho-position with respect to the nitrogen atoms, the peroxycarboxylation of R may be carried out also, a product of formula (I) with two or more peroxycarboxylic groups being thus obtained.

According to a preferred embodiment, the peroxycarboxylation of the heterocyclic carboxylic acids used as the starting substrate, or of the esters or anhydrides thereof, is carried out by gradually adding $H_2O_2$ (having approximately a concentration of from 70% to 90% by weight) to a solution of the substrate in $H_2SO_4$ or $CH_3SO_3H$, the reaction temperature being approximately maintained, throughout the course of the reaction, from 15° to 50° C., according to the reactivity of the substrate.

Alternatively, it has been found to be advantageous to prepare in advance the salt of the substrate (in the form of an $HSO_4^-$ or a $CH_3SO_3$ salt), by processing under the same conditions as mentioned above, but in the absence of $H_2O_2$, and then by separating and peroxidizing the thus-obtained salt to the compound of formula (I).

The amount of $H_2SO_4$ or of $CH_3SO_3H$, computed at 100% concentration, is from 3 to 30 moles per mole of substrate, and preferably from 7 to 10 moles per mole of substrate.

The amount of hydrogen peroxide is in excess with respect to the substrate and is approximately 1.2 to 6 moles per mole of substrate, and preferably from 3 to 4 moles per mole of substrate.

The reaction time depends on the nature of the substrate, on the operating temperature, and on the total $H_2SO_4/H_2O$ or $CH_3SO_3H/H_2O$ molar ratios present at the end of the reaction. Said ratios are approximately from 1.0 to 10, and preferably from 3 to 7, achieved by adjusting the various parameters.

Reaction times approximately within the range of from 30 minutes to 4 hours have proved to be satisfactory, and generally a reaction time approximately from 1 hour to 2 hours has proved to be quite sufficient.

The amount of tetrahydrofuran or ethyl acetate to be used as solvent is usually not lower than 4 liters per mole of substrate; furthermore, it is added at a temperature not higher than approximately 10° C.

The heterocyclic peroxycarboxylic acids having formula (I) are usually solid at room temperature; they may be used particularly in detergent formulations, e.g., in granular formulations, as bleaching agents in solution over a wide temperature range, thanks to their good storage stability and their good thermal stability in the as-obtained condition. The detergent compositions may be formulated according to the usual techniques, together with other components and/or additives well known per se in the detergent art.

Moreover, the final reaction mixture, before separation of the (poly)peroxycarboxylic acids of formula (I) may be subjected to a phlegmatization process.

This invention will now be further described in still greater detail in the following examples, which are supplied for purely illustrative and non-limiting purposes.

The products prepared in the examples were characterized by elemental analysis, by determining their content of active oxygen (by iodometric nitration), and by FT-IR spectroscopy (FT-IR=Fourier Transform Infrared Spectroscopy).

EXAMPLE 1

Into a beaker, equipped with stirrer, thermometer, and outer bath, 15 g (0.156 moles) of methanesulfonic acid were introduced. The internal temperature was maintained from 10° to 15° C. and 3 g (0.0225 moles) of 4-piperidine-carboxylic acid were added under stirring.

To the clear solution 1.56 g of 70% $H_2O_2$ (0.0321 moles) were gradually added in such a way as to keep the temperature constantly around 15° C.; the stirring went on at this temperature for 30 minutes. The reaction mixture was then poured into 100 cm³ of tetrahydrofuran, the solution being stirred at 10° C. After a few minutes, the products separated in the crystalline form. Stirring went on for 1 hour at a temperature from 0° to 10° C., then the solution was filtered under vacuum over a porous glass filter. The product was directly washed on the filter with tetrahydrofuran (20 cm³), then with ethyl ether (30 cm³). The product was then placed in a $CaCl_2$-dryer under vacuum and at room temperature for 1 hour. 4.7 g of crystalline, practically pure 4-piperidine-peroxycarboxylic acid methanesulfonate were obtained (yield=85%).

Elemental Analysis Computed for $C_{17}H_{14}O_6NS$: C: 34.80%; H: 6.26%; N: 5.80%; (active) 0: 6.67%; $CH_3SO_3H$: 39.8%.

Found: C: 34.84%; H: 6.30%; N: 5.72%; (active) 0: 6.60%; $CH_3SO_3H$: 40.0%.

Melting point: 92° C. (with decomposition).

EXAMPLE 2

1.7 g of monohydrated ethylisonipecotic acid (0.0097 moles) were dissolved at room temperature in 12 g of $CH_3SO_3H$ (0.125 moles). The internal temperature was maintained at 20° C. and 1.6 g of 85% $H_2O_2$ (0.04 moles) were added.

After 30 minutes, while stirring at 20° C., the reaction mixture was poured into 100 cm³ of ethyl aceta at 10° C. A heavy oily product separated. After 30 minutes of stirring at 10° C., ethyl acetate was decanted off. The product was washed, still by decantation, with 2×120 cm³ of tetrahydrofuran and with 100 cm³ of ether. The product was then thoroughly dried under vacuum in a dryer at room temperature for approximately 1 hour.

2.5 g were thus obtained of a colorless oily product having an oxygen content of 5.16% (87% when expressed as N-ethyl-piperidine-4-peroxycarboxylic acid methanesulfonate). The yield was (approximately) 83%.

EXAMPLE 3

Into a beaker equipped with stirrer, thermometer, and outer bath, 15 g (0.147 mole) of 96% sulfuric acid were loaded. The internal temperature was maintained from 10° to 15° C. and 6 g (0.0450 mole) of 4-piperidinecarboxylic acid were added under stirring.

To the clear solution 6 g of 70% $H_2O_2$ (0.123 moles) were gradually added in such a way as to keep the temperature constantly around 15° C.; the stirring went on at this temperature for 30 minutes. The reaction mixture was then poured into 200 cm³ of ethyl acetate, the solution being stirred at −5° C. After a few minutes, the products separated in crystalline form. Stirring went on for 30 minutes at a temperature of −5° C., then the solution was filtered under vacuum over a porous glass filter. The product was directly washed on the filter with ethyl acetate (30 cm³), and then with ethyl ether (30 cm³). The product was then kept inside a $CaCl_2$-dryer under vacuum and at room temperature for 1 hour. 9 g of crystalline, practically pure 4-piperidine-peroxycarboxylic acid sulfate were obtained (yield=80%).

Elemental Analysis:

Computed for $C_6H_{13}O_7NS$: C: 29.62%; H: 5.38%; N: 5.76%; (active) 0: 6.57%;

Found: C: 29.87%; H: 5.40%; N: 5.73%; (active) 0: 6.55% $H_2SO_4$: 39.81%.

Melting point: 47° C. (with decomposition).

EXAMPLE 4

2 g of N-pentyl isonipecotic acid (0.0068 moles) were dissolved at 30° C. temperature in 5.5 g of $CH_3SO_3H$ (0.057 moles). The internal temperature was maintained at 15° C. and 0.35 g of 85% $H_2O_2$ (0.0088 moles)

After 30 minutes stirring at 15° C., the reaction mixture was poured into 70 cm³ of a 1:1 mixture of ethyl ether/ethyl acetate kept stirred at −10° C. A heavy oily product separated. After 30 minutes of stirring at −10° C. solvent was decanted off. The thus-obtained oil was dissolved in 10 cm³ of anhydrous ethanol and the crystalline product was precipitated by adding, under stirring, to the solution 50 cm³ of ethyl ether, at room temperature. The mixture was filtered under vacuum, and dried in a dryer at room temperature throughout 1 hour under vacuum. The product was washed, still by decantation, with 2×100 cm³ of tetrahydrofuran and with 100 cm³ of ethyl ether. The product was then thoroughly dried under vacuum in a dryer at room temperature for approximately 1 hour.

1.4 g were thus obtained of N-pentyl-piperidine-4-peroxycarboxylic acid methanesulfonate having an active oxygen content of 4.73% (equals 92%) (yield 61%).

Elemental Analysis

Computed for $C_{12}H_{25}O_6NS$: C: 46.28%; H: 8.09%; N: 4.49%; $CH_3SO_3H$: 30.86%.

Found: C: 45.74%; H: 8.12%; N: 4.37%; $CH_3/SO_3H$: 30.71%.

Melting Point: 53° C. (with decomposition).

EXAMPLE 5

Into 13 g of $CH_3SO_3H$ (0.135 moles) there were dissolved, at room temperature, 4 g of N-methylnipecotic acid methanesulfonate (0.0167 moles). Processing according to Example 4, there were added 0.8 g of 85% $H_2O_2$ (0.02 moles), and stirring went on at 15° C., for 30 minutes. The reaction mixture was then poured in 150 cm³ of ethyl acetate, kept under stirring at 0° C., and, by proceeding as in Example 4, a thick oil separated which crystallized from ethanol/ethyl ether. There were obtained 2 g of N-methylpipe-ridine-3-peroxycarboxylic acid methanesulfonate, having an active oxygen content of 6.0% (equal to 95.84%) (yield 46%).

Elemental Analysis

Computed for $C_8H_{17}O_6NS$: C: 37.64%; H: 6.71%; N: 5.48%; $CH_3SO_3H$: 37.64%.

Found: C: 37.91%; H: 6.97%; N: 5.61%; $CH_3SO_3H$: 37.84%.

Melting Point: 54° C. (with decomposition).

EXAMPLE 6

By proceeding according to Example 5, 4.2 g (0.0115 moles) Of N-decyl-isonipecotic acid methanesulfonate were dissolved in 4.2 g (0.0437 moles) of $CH_3SO_3H$, and then 0.75 g 88 moles) of 85% $H_2O_2$ were added, under further stirring at 15° C., or 45 minutes. The reaction mixture was then poured into 100 cm³ of tetrahydrofuran, kept under stirring at −5° C. Then, by proceeding as in Example 3, there were isolated 3.5 g of N-decyl-piperidine-4-peroxycarboxylic acid methanesulfonate, in a practically pure crystalline form (yield 80%).

Elemental Analysis

Computed for $C_{17}H_{35}O_6NS$: C: 53.51%; H: 9.24%; N: 3.67%; O (active): 4.19%; $CH_3SO_3H$: 25.19%.

Found: C: 53.4%; H: 9.04%; N: 3.61%; 0 (active): 4.18% $CH_3SO_3H$: 24.91%.

Melting Point: 100° C. (with decomposition).

EXAMPLE 7

By proceeding according to Example 4, 2 g (0.0057 moles) of N-hexadecylisonipecotic acid were dissolved in 7.2 g (0.0749 moles) of $CH_3SO_3H$, and then 0.3 g (0.0075 moles) of 85% $H_2O_2$ were added, under further stirring at 15° C. for 30-minutes.

The reaction mixture was then poured into 50 cm$^3$ of ethyl acetate, kept under stirring at 0° C. Then, by proceeding as in Example 3, there were isolated 2 g of N-hexadecylpiperidine-4-peroxycarboxylic acid methanesulfonate, in a practically pure crystalline form (yield 75%).

Elemental Analysis

Computed for $C_{23}H_{47}O_6NS$: C: 59.32%; H: 10.17%; N: 3.00%; O (active): 3.43%; $CH_3SO_3H$: 20.63%.

Found: C: 58.90%; H: 9.86%; N: 2.88%; 0 (active): 3.42% $CH_3SO_3H$: 20.32%.

Melting Point: 104° C. (with decomposition).

EXAMPLE 8 (Bleaching Performance)

Bleaching tests were carried out with the new nitrogen-containing heterocyclic peroxyacid showing a saturated structure, and identified as 4-piperidine-peroxycarboxylic acid methanesulfonate, as compared to:

(a) H 48 (Mg salt of monoperphthalic acid), a commercial peroxyacid known in the field of detergency, manufactured by INTEROX Chemical Ltd., London, U.K.

(b) A perborate+activator system, which, as is known, gives rise to a peroxyacid (peracetic acid) in situ when both products are dissolved in water, and which represents the currently most widely marketed form for the purpose of obtaining a bleaching action at medium-low temperatures (60° C.), wherein as the activator, TAED (tetraacetylethylenediamine) was selected, in an amount corresponding to the stoichiometric ratio with respect to the perborate.

(c) Tetrahydrated sodium perborate ($NaBO_3.4H_2O$) alone.

All the tests were carried out at a constant temperature of 60° C., with an initial concentration of total active oxygen in the bleaching solution equal for all products (200 mg/liter).

Process

For each test, 500 cm$^3$ of deionized water, contained in a flask of 1,000 cm$^3$ flask equipped with a cooler, was heated at a temperature of 60° C. and its pH value was adjusted to 9.5 with a few drops of NaOH solution, and then the bleaching product was added under stirring, the amounts being shown in the following Table 1. Thereafter were added immediately two cotton specimens of 10 cm × 10— cm, stained with standard stains of red wine at the EMPA Institute of St. Gallen (Switzerland), marked as "EMPA 114".

The system was subsequently kept 60 minutes under stirring and, at the end of this time, the specimens, rinsed under running water, were dried and ironed and were then submitted to an evaluation of the bleaching effect (by measuring the degree of whiteness by reflectometry).

$$\text{Bleaching \%} = \frac{A - B}{C - B} \times 100$$

wherein:

A=degree of whiteness (%) of the specimen bleached during the test;

B=degree of whiteness (%) of the specimen before the test;

C=degree of whiteness (%) of the completely bleached specimen, and wherein the degrees of whiteness were measured by means of an Elrepho Zeiss reflectormeter, assuming MgO=100% of whiteness and using filter N6 ($\lambda$464 nm).

The data thus obtained show that the new peroxyacid has a bleaching power that is significantly higher than the bleaching power of all of the other tested bleaching agents.

TABLE 1

| Bleaching Agent | Amount used in the tests (grams) | Initial concentration of total active oxygen (mg/l) | Bleaching % |
|---|---|---|---|
| 4-Piperidine-peroxy-carboxylic acid methane-sulphonate (titer = 6.6% of active oxygen) | 1.56 | 200 | 83 |
| H 48 (titer = 5.5% of active oxygen) | 1.86 | 200 | 82.1 |
| Perborate tetrahydrate (titer = 10% of active oxyen + TAE:D (titer = 93%) | 1.0 + 0.8 | 200 | 79.7 |
| Perborate tetra-hydrate (titer = 10% of active oxygen) | 1.0 | 200 | 68.8 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A nitrogen-containing heterocyclic (poly)peroxycarboxylic acid having the formula:

$$(R)_m \underset{\underset{R_1}{|}}{\overset{(CH_2)_n}{\diagdown N \diagup}} C\text{—OOH} \quad .HX \qquad (I)$$
$$\qquad\qquad\qquad\qquad \| \\ \qquad\qquad\qquad\qquad O$$

wherein the symbols have the following meanings:

R and $R_1$ represent, independently of each other, a hydrogen atom or a straight or branched alkyl, (hetero)-cycloalkyl, (hetero)aryl, alkylaryl or arylalkyl group, optionally substituted, a carboxylic, or any other substituent which is non-reactive in the presence of the active oxygen of the peroxycarboxylic group;

n is an integer selected from 0, 1 and 2;

m is an integer selected from 0, 1, 2 and 3, and represents an acidic anion selected from H $SO_4^-$ and $CH_3SO_3^-$;

and wherein the heterocyclic may optionally be condensed with at least one further (hetero)aromatic or (hetero)cycloalkyl ring.

2. A heterocyclic (poly)peroxycarboxylic acid having formula (I) according to claim 1, wherein R and/or $R_1$ are selected from a linear or branched alkyl, (hetero)aryl, (hetero)-cycloalkyl, alkyl-aryl or arylalkyl group, containing an overall number of up to 10 carbon atoms, optionally having at least one substituent selected from F, Cl, $NO_2$, lower ($C_1$-$C_5$)-alkoxy groups, or at least one carboxylic group, an F atom, a Cl atom, a lower ($C_1$-$C_5$)-alkoxy group, wherein the heteroatoms are selected from N and O.

3. A (poly)peroxycarboxylic acid according to claim 2, wherein the heterocyclic ring consists of a ring condensed with at least one other pyridinic, (hetero)aromatic, or (hetero)cycloalkyl ring.

4. As a per se new compound: 4-piperidineperoxycarboxylic acid methanesulfonate.

5. As a per se new compound: N-ethyl-piperidine-4-peroxycarboxylic acid methanesulfonate.

6. As a per se new compound: 4-piperidine-peroxycarboxylic acid sulfate.

7. As a per se new compound: N-pentyl-piperidine-4-peroxycarboxylic acid methanesulfonate.

8. As a per se new compound: N-methyl-piperidine-3-peroxycarboxylic acid methanesulfonate.

9. As a per se new compound: N-decyl-piperidine-4-peroxycarboxylic acid methanesulfonate.

10. As a per se new compound: N-hexadecyl-piperidine-4-peroxycarboxylic acid methanesulfonate.

11. A nitrogen-containing heterocyclic (poly)peroxycarboxylic acid having a stable solid form and having the formula:

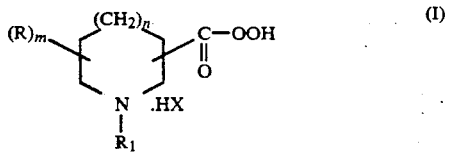

wherein the symbols have the following meanings:
R and $R_1$ represent, independent of each other, a hydrogen atom or a straight or branched alkyl, (hetero)-cycloalkyl, (hetero)aryl, alkylaryl or arylalkyl group, optionally substituted, a carboxylic, or any other substituent which is non-reactive in the presence of the active oxygen of the peroxycarboxylic group;
n is an integer selected from 0, 1, and 2;
m is an integer selected from 0, 1, 2, and 3, and
X represents an acidic anion selected from $HSO_4^-$ and $CH_3SO_3^-$;
and wherein the heterocyclic ring may optionally be condensed with at least one further (hetero)aromatic or (hetero)cycloalkyl ring.

12. A process for preparing a heterocylic (polyperoxycarboxylic acid having the formula (I), as defined in claim 1, wherein a substrate constituted by a heterocyclic (poly)carboxylic acid and/or its anhydride and/or its lower alkyl esters, corresponding to the desired peroxycarboxylic acid having formula (I), is reacted with concentrated $H_2O_2$, by operating in a medium selected from concentrated $H_2SO_4$ and $CH_3SO_3H$ and in that the peroxycarboxylic acid (I) is then separated from the reaction mixture by insolubilization caused by addition of an organic solvent selected from tetrahydrofuran and ethyl acetate.

13. A process for preparing a heterocyclic (poly)-peroxycarboxylic acid having the formula (I), as defined in claim 1, wherein a substrate constituted by a heterocyclic (poly)carboxylic acid and/or its anhydride and/or its lower alkyl esters, corresponding to the desired peroxycarboxylic acid having formula (I), is converted into its $HSO_4^-$ and $CH_3SO_3^-$ salt which is then reacted with $H_2O_2$ in concentrated $H_2SO_4$ and $CH_3SO_3H$, by separating the obtained heterocyclic (poly),peroxycarboxylic acid of formula (I) by the addition of an organic solvent selected from tetrahydrofuran and ethyl acetate.

14. A process according to claim 12 or 13, wherein the substrate is constituted by a straight or branched ($C_1$-$C_5$)-alkyl ester of the heterocyclic (poly)peroxycarboxylic acid of formula (I).

15. A process according to claim 12 or 13, wherein the substrate is constituted by an anhydride of a heterocyclic dicarboxylic acid corresponding to the desired (poly)peroxycarboxylic acid of formula (I).

16. A process according to claim 12 or 13, characterized in that the substrate is selected from the class consisting of 4-piperidine-carboxylic acid, 2,4-piperidinedicarboxylic acid, 3-piperidine-carboxylic acid, 2,3-piperidine-dicarboxylic acid and its anhydride, 2,5-piperidine-dicarboxylic acid, 3,5-piperidine-dicarboxylic acid, the ethyl ester of 4-piperidine-carboxylic acid, 2,6-dihydroxy-4-piperidine-carboxylic acid, 6-isobutyl-3-piperidine-carboxylic acid, 6-methyl-3-piperidine-carboxylic acid, 6-fluoromethyl-3-piperidine-carboxylic acid, 5-p-tolyl-piperidine-carboxylic acid, 5-benzyl-3-piperidine-carboxylic acid, 5-chloro-4-piperidine-carboxylic acid, and 3-pyrrolidine carboxylic acid.

17. A process according to claim 12 or 13, wherein the heterocyclic (poly)peroxycarboxylic acid substrate, its anhydride, or its lower-alkyl ester is gradually reacted with $H_2O_2$, which has approximately a concentration of 70% to 90% by weight, in concentrated $H_2SO_4$ or $CH_3SO_3H$ at a temperature approximately between 15° to 50° C.

18. A process according to claim 12 or 13, wherein the amount of $H_2SO_4$ or $CH_3SO_3H$ is approximately from 3 to 30 moles, and preferably from 7 to 10 moles, per mole of substrate.

19. A process according to claim 12 or 13, characterized in that the amount of hydrogen peroxide is approximately 1.2 to 6 moles, and preferably from 3 to 4 moles, per mole of substrate.

20. A process according to claim 12 or 13, wherein the end molar ratio of $H_2SO_4$ or $CH_3SO_3H$ to the total $H_2O$ present at the end of the reaction is approximately 1.0 to 10, and preferably from 3 to 7.

21. A process according to claim 12 or 13, wherein the amount of tetrahydrofuran or of ethyl acetate used as a solvent is not less than 4 liters per mole of substrate.

22. A process according to claim 12 or 13, wherein tetrahydrofuran or ethyl acetate is added at a temperature not higher than approximately 10° C.

23. A detergent formulation comprising a bleaching effective amount heterocyclic nitrogen-containing (poly)peroxycarboxylic acid having the formula (I) of claim 1 as a bleaching agent.

* * * * *